United States Patent [19]

Chance

[11] Patent Number: 5,062,428

[45] Date of Patent: Nov. 5, 1991

[54] METHOD AND DEVICE FOR IN VIVO DIAGNOSIS DETECTING IR EMISSION BY BODY ORGAN

[75] Inventor: Britton Chance, Philadelphia, Pa.

[73] Assignee: Nim Incorporated, Philadelphia, Pa.

[21] Appl. No.: 653,971

[22] Filed: Feb. 11, 1991

Related U.S. Application Data

[63] Continuation of Ser. No. 532,142, Jun. 4, 1990, abandoned, which is a continuation of Ser. No. 149,551, Jan. 28, 1988, abandoned.

[51] Int. Cl.[5] .............................................. A61B 6/00

[52] U.S. Cl. .................................... 128/664; 128/665

[58] Field of Search .................. 128/202.72, 664, 665, 128/DIG. 72; 600/3, 2

[56] References Cited

U.S. PATENT DOCUMENTS

| | | | |
|---|---|---|---|
| 2,358,992 | 9/1944 | Millikan . | |
| 2,640,389 | 6/1953 | Liston . | |
| 2,804,069 | 8/1957 | Schwamm et al. | 128/664 |
| 3,948,249 | 4/1976 | Ambrosini . | |
| 3,961,627 | 6/1976 | Ernst et al. | 128/202.22 |
| 4,041,932 | 8/1977 | Fostick . | |
| 4,350,166 | 9/1982 | Mobarry . | |
| 4,414,980 | 11/1983 | Mott . | |
| 4,534,360 | 8/1985 | Williams . | |
| 4,550,726 | 11/1985 | McEwen | 128/202.22 |
| 4,592,361 | 6/1936 | Parker et al. | 128/654 |
| 4,646,750 | 3/1987 | Williams . | |

OTHER PUBLICATIONS

Szeles, D. M., "Biotherapy in the 8- to 14-Micron Spectral Region", Proc. Biomed. Sci. Instr. Symp. Ann Arbor, Mich. USA (19-22, 1969).

Direct Spectroscopic Observation of Singlet Oxygen Emission at 1268 nm Excited by Sensitizing Dyes of Biological Interest in Liquid Solution, A. U. Khan & M. Kasha, Proc. Natl. Acad. Sci. USA, vol. 76, No. 12, pp. 6047-6049, Dec., 1979.

Chance et al, "Hydroperoxide Metabolism in Mammalian Organs", vol. 59, No. 3, Jul. 1979.

Jane E. Brazy, MD et al., "Noninvasive Monitoring of Cerebral Oxygenation in Preterm Infants: Preliminary Observations", vol. 75, Feb. 1985, No. 2.

*Primary Examiner*—Francis Jaworski
*Assistant Examiner*—Scott R. Akers
*Attorney, Agent, or Firm*—Browdy and Neimark

[57] ABSTRACT

A sensitive photon detector can be used for external detection in vivo of emission from a body organ, for instance of singlet oxygen emission in the near infrared at 1280 nm, for various purposes such as control of oxygenation of a patient. At such a wavelength bone and overlying tissue are sufficiently transparent to allow detection exteriorly of the body. Stray light and thermal emissions at this wavelength in a lit room are sufficiently low, or can otherwise be controlled, to allow detection of this singlet radiation by for instance a cooled Ge detector, to determine a rate of detected photons. Detection of this radiation can be taken for instance as indicating damage in process from overoxygenation of a patient, allowing preventing and remedial measures to be taken in oxygen treatment. If a wavelength of interest is absorbed by overlying body tissues, insertion of an optical fiber leading to a detector, or of a detector itself, into the patient's body via a cavity of the body or otherwise can be employed for getting sufficiently close to the organ of interest.

19 Claims, 2 Drawing Sheets

METHOD AND DEVICE FOR IN VIVO DIAGNOSIS DETECTING IR EMISSION BY BODY ORGAN

This application is a continuation of application Ser. No. 07/532,142 filed June 4, 1990 now abandoned which was a continuation of application Ser. No. 07/149,551, filed Jan. 28, 1988, now abandoned.

BACKGROUND OF THE INVENTION

The field of the present invention involves external observations of internally generated emissions of electromagnetic radiation, for instance observation of singlet oxygen generation in body organs by infrared fluorescence spectroscopy, and the use of such observations for related diagnosis and therapy. Emissions from a body organ, indicative of its status or of processes occurring in it, and which are transmitted through overlying tissues, are detected such as for control of oxygen therapy.

It is known from analytical chemistry laboratory work that when a reaction in a solution produces or releases singlet oxygen, the solution can effectively glow in, for instance, the infrared region of the electromagnetic spectrum. It has also been known that infrared wavelengths are somewhat transparent through tissue and bones. The prior art has suggested observing deviations from thermal black-body radiation for medical diagnosis (U.S. Pat. No. 2,804,069). Other prior art has involved black-body radiation from localized external areas of an animal's body (U.S. Pat. No. 3,948,249), or absorption or reflection in human tissue of externally-supplied radiation (see for example U.S. Pat. Nos. 2,358,992, 2,640,389, 4,041,932, 4,350,166, 4,414,980). Chemiluminescence has also been detected in human breath, and from internal tissues, for detection of lung cancer, etc., as in U.S. Pat. Nos. 4,534,360 and 4,646,750 to Williams.

Previously, it has not been possible to determine the presence of singlet oxygen in the human body, as it is a rather transient molecule. It is known, however, that singlet oxygen and other species involving unreduced oxygen are toxic. (See for example "Hydroperoxide Metabolism in Mammalian Organs", Chance et al, *Physiological Reviews*, July 1979, pp 527–605.)

SUMMARY OF THE INVENTION

A purpose and object of the present invention is the external detection of internally-generated radiation from a part of interest in a human body.

A further purpose of the present invention is to diagnose a condition of a body organ in vivo by detecting infrared radiation emitted in the organ and transmitted through a superficial layer of body tissue and/or bone.

A further purpose of the present invention is to detect the occurrence of a process occurring in a body organ in vivo by detecting infrared radiation emitted therein and transmitted through a superficial layer of body tissue and/or bone, or detected by intrusion via a body cavity.

A further object of the invention is to determine the state of a living organ by detecting photons of electromagnetic radiation characteristically emitted from the organ at higher than thermal radiation levels. A detector is located outside the body for wavelength regions as to which the overlying tissues and/or bone are sufficiently transparent. Intrusion of at least part of a detector in a body cavity or region may be used for wavelengths as to which the overlying tissues are not sufficiently transparent.

A further object of the present invention is a process which an emission of interest from a body organ can be monitored for the purposes of the present invention even if that wavelength is not adequately transmitted through overlying body tissues and bone, by intrusion of at least a part of the detector such as optic fibers via a body cavity.

A further object is monitoring the 1268 nm singlet oxygen emission for controlling the amount of oxygen being supplied to a patient, after a stroke or other hypoxic event. The absolute value of the amount of the singlet emission is used to regulate oxygen administered.

A further object is to use the observed change in any such detected emission from a body organ, or relative rate of emission of the organ with respect to any other part of the patient's body, to determine information concerning the state of the emitting organ, or concerning a process occurring therein, for diagnosis or therapeutic purposes.

DETAILED DESCRIPTION OF PREFERRED EMBODIMENT

The invention relates to determining the status of or processes occurring in living body organs from photons emitted therefrom, such as due to specific chemical reactions occurring in the organ, by a photon detector located outside the body, in a wavelength region not obscured by thermal emissions and not totally absorbed by overlying body layers. Alternately, such as when the emission is very weak or at a wavelength greatly absorbed by overlying tissue and bone, a part of the detector for receiving the photons of the emission can be intruded into the body.

The present invention particularly involves detection of a specific emission at about 1,268 nm from singlet molecular, oxygen, for instance as an indicator of damage in the process occurring due to excess oxygenation following oxygen deprivation, to allow preventive and remedial action to be taken.

A preferred embodiment of the present invention is the use of an infrared sensitive photon counting detector in order to provide a photon counting rate for singlet oxygen emission from the human body for the purpose of various diagnostic and therapeutic techniques. According to the present invention, monitoring for the optimization of oxygen therapy in humans is possible. When pure oxygen is being administered, singlet oxygen is generated when, for instance, the brain receives too much oxygen. If the eyes, lungs and/or brain are monitored with an infrared sensitive photon counting detector, the generation therein of singlet oxygen can be monitored and once it is detected, the pure oxygen therapy can be stopped or the treatment can be otherwise altered or other action taken.

Figure 1:
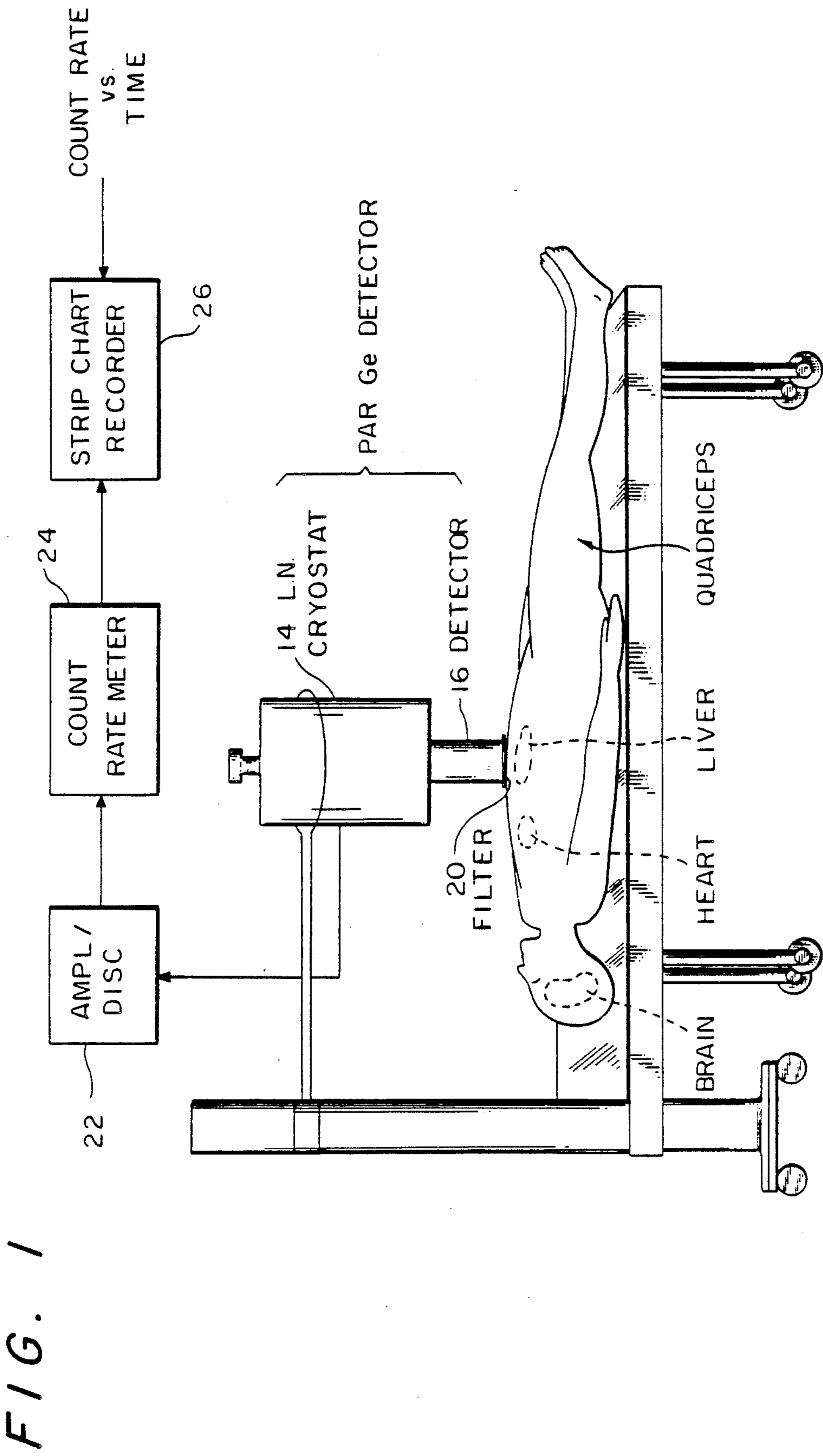
FIG. 1 indicates the monitoring of singlet oxygen emission from the liver of a patient, by a cooled detector providing output pulses corresponding to detected photons to an optical discriminator and a count-rate meter for recording count rate.

The present invention is exemplified by the embodiment indicated in FIG. 1. The singlet oxygen emission at 1,268 nm from an organ in a living patient is being observed in an examination room. In this case it is the liver that is shown to be under observation. With the illustrated equipment, this observation can occur in normal room light.

The patient whose liver is emitting this radiation lies prone, and pressed against the margin of his liver from the exterior of the patient's body is a germanium detector 16 maintained in a cryostat 14 at liquid nitrogen temperatures for optimal sensitivity. A window of this detector 16 can be sealed to the patient's abdomen with masking tape. Alternately a filter 20 can be provided to prevent visible light from impinging on the detector, or an IR bandpass filter can be provided to define a narrow bandpass about the wavelength of interest. For protection from visible room light, for instance, a Corning CS 7-56 filter can be used, which at the emission of interest in the near infrared has a transmission of approximately 50%.

The germanium detector 16 is connected to an appropriate amplifier to constitute a cooled Ge detector as indicated. Each output of the detector 16 corresponds to a photon from the $1\Delta_g - 3\Sigma_g$ transition of molecular oxygen in the organ of interest.

The output events from the PAR detector are provided to a pre-amplifier 22 which can also act as a discriminator, and the output of the pre-amplifier 22 is provided to a count rate meter 24 for determining the rate of the photon counts. The count rate is provided to the strip chart recorder 26, to provide a record of count rate versus time. The information in the count rate can thus be appraised while any change is occurring, or based on its absolute value, to provide an indication of the status of the organ or change or process occurring therein.

A protocol for such biological measurements of a patient's organs is to examine the organ of interest, such as the heart, kidney and/or brain, while using, for instance, a similar or the same emission from the thigh (or quadricep) muscle as a reference or control level. Alternatively, the absolute value of the emission of interest can be useful, such as for determining the actual amount of an undesirable radical being produced in the organ of interest, such as for the preferred embodiment above using the infrared emission from singlet oxygen.

Studies based on such emissions can be divided into different categories of disease. For the liver, such diseases would include alcoholism and hepatitis. Such diseased conditions can be expected to alter the liver's production of molecular oxygen in the singlet state.

With respect to the heart and brain, recovery from stroke and heart attack are of special interest, since reflow of oxygen into previously ischemic regions is expected to cause lipid peroxidations and singlet oxygen production. (See Chance et al above and U.S. Pat. Nos. 4,534,360 and 4,646,750 to Williams on these and other relevant points on the context from which the present invention arises and operates.)

The present invention thus involves measuring singlet oxygen emission in the body tissues with an appropriate photon counter over the brain, liver, kidney, etc. areas, with appropriate controls on skeletal tissues. Such determinations can be done in animal models under a variety of hyperoxic, hypercapnic and even particular $H_2O_2$ conditions. Human patients with histories of smoking, cancer, and particularly diseases which involve membrane degradation, are particularly of interest.

Figure 2:
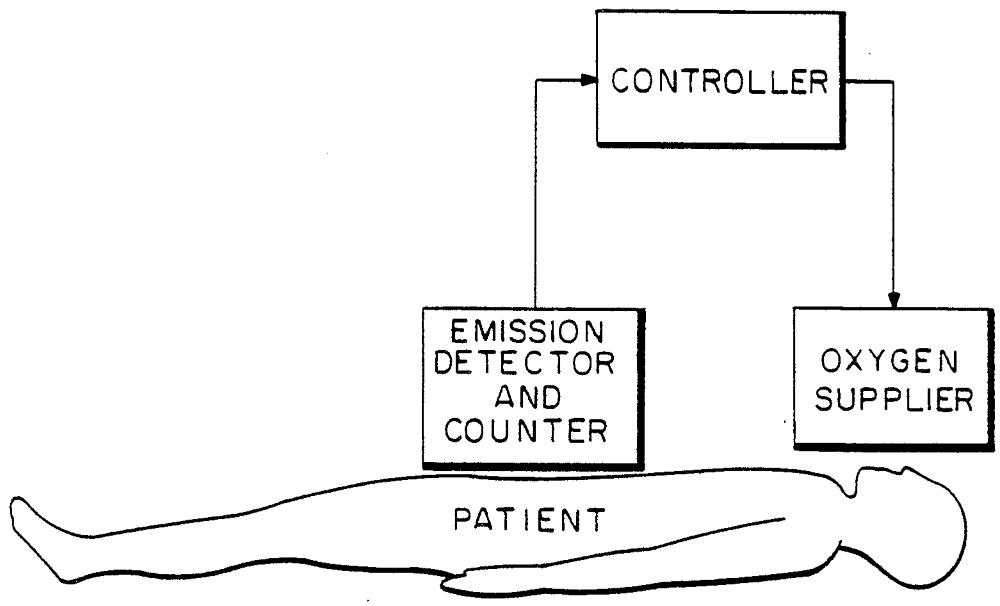
FIG. 2 indicates use of emission from a body organ, detected externally of the patient, for control of oxygen supply to the patient.

Thus, a pure oxygen therapy system can be provided with an infrared detection means specifically limited to the frequency band generated by the singlet oxygen in the infrared, including means to control the supply of pure oxygen in accordance with the level of the singlet oxygen radiation emitted from the patient's tissue. This is indicated in FIG. 2, showing control of oxygen supplied to a patient by the amount of detected emission at the wavelength of interest.

A general protocol could be used for examining intoxication, for instance by paraquat. This organic chemical is known to have a singlet-producing effect with respect to oxygen in the human body, and is sometimes taken as a suicide drug. After ingestion of this chemical, examinations of the blood and all target organs (especially the lungs) would be of interest, to follow the development and prognosis of the effects on the patient.

The detection of low levels of such chemiluminescent radiation can be difficult, but embodiments of the present invention can take advantage of the laws of physics that the number of photons reaching the detector depends upon the volume of tissue emitting the radiation of interest and the area of the detector receiving such radiation. Thus, the liver of the adult human may measure over 10 inches across, and provide a very high total photon flux. The specific embodiment of a germanium detector disclosed above is intended to indicate the general characteristics of the detector, and specifically to emphasize that the area of the detector can be increased to match that of the surface of the liver projected through the stomach wall onto the detector. Further development of low level detectors may provide great simplification, for instance as the sensitivity and threshold of germanium and silicon diode detectors is increased. A 13-element detector covering a 50 cm diameter is now available.

Similar advantages according to the present invention arise with respect to the head and chest regions, where the brain or lung tissue might be expected to emit under conditions of recovery from stroke and hyperoxic damage due to paraquat, respectively.

Technical problems involved in picking up red (shorter wavelengths extending down into the visible region) radiation, such as from dimol emission, epoxide bond breaking, etc., are vastly different than for wavelengths less absorbed by intervening body tissues, except possibly for the case of the eye of an adult, and the neonate brain where the thin cranium, or the poorly developed musculature over the liver, allows or enhances the direct detection of such wavelengths. An extended silicon diode array in the form of goggles for the eyes or a cap or girdle provides very sensitive detection for such red and infrared radiation according to the present invention.

The detection of such infrared and red radiation from the adult brain, heart, liver, intestines, etc. is further proposed according to the present invention to be accomplished by fiber optics catheterization of appropriate zones of the body. Here, the catheter size is generally limited by the diameter of the orifice, for instance a diameter of several cm is possible for the anal region. For the nasal region, where penetration to the base of the brain is possible, for instance 1–2 mm in some cases in each nostril is feasible. In cases involving use of a small-area silicon detector, or where the signals are smaller, a highly sensitive electron multiplier phototube of very low background count (1-2 per second) could be employed.

While movement of the patient will generally not interfere with the chemiluminescent detection in the anal or vaginal regions, on the other hand modest sedation is typically advisable for intrusion of, for example, the nasal region.

Such a methodology for diagnosis of organs in vivo, according to a preferred embodiment disclosed above, relies upon the fact that singlet oxygen emits radiation when undergoing the singlet-to-triplet transition at a wavelength (1268 nm) that readily penetrates overlying tissues and even bone. Thus, the emission of this radiation at the deepest tissue depths can be readily detected. A sensitive germanium detector thus enables evaluation of the extent of singlet oxygen production in organs, which can be used both as a general diagnostic tool and for control of therapeutic treatments.

As already noted above, since the thin skin of a newborn baby transmits visible light as well as infrared light, the same approach described above with regard to singlet oxygen emission in the infrared could be applied as to other wavelengths of interest, such as from molecules and states other than singlet molecular oxygen. The present invention can thus be generally regarded as involving tissue translucency to emissions from the organs themselves, or methodology involving direct access to the organ or tissue of interest via a body cavity or via a body region to be penetrated such as with fiber optics, etc.

In the present invention, the sensor is not used to detect the level of oxygen itself, but more importantly enables determination of the deleterious affects of oxygen upon the tissue of interest due to the generation of toxic free radicals in the form of singlet oxygen, dimol oxygen, peroxide bond rupture and bond rupture of epoxides of various fats, etc. Thus, the methodology according to the present invention has an advantage over known methodology wherein an oxygen supply level is simply set to a predetermined value that is hoped to provide a safeguard that the oxygen levels being administered do not exceed critical values for generation within the body of such harmful radicals.

Instead of direct detection of the singlet oxygen line at 1.28 microns, the present invention can employ a detector that is sensitive to yet shorter wavelengths emitted as a result of or in association with this particular singlet oxygen line.

Relevant medical and biochemical factors and treatments include generally recovery from ischemic tissue damage (such as from the above-noted reflow phenomenon following a hypoxic ischemic interval or following ingestion of toxic chemicals that enhance radical generation, for instance ingestion of the herbicide paraquat noted above to be often taken in suicide attempts) and any other process which leads to a pathological evolution of radical species.

The present invention has as objects or involves among its features the following: a) direct observation of infrared or visible radiation from any emitting organ lying within or at the surface of the body, as detected by its transmission through the superficial tissue; or b) a fiber optics coupling to a target organ with catheterization or impingement through any orifice of the body, particularly the nasal cavity for the brain or anal/vaginal cavities for other organs located centrally.

The above description of various embodiments is intended as exemplary only, and not to be limiting in any regard. Various extensions and modifications of the present invention would be understood by a skilled worker in the art in possession of the present disclosure.

What is claimed is:

1. A method for in vivo monitoring of the condition of an internal body organ of a patient, comprising:

detecting photons of electromagnetic radiation caused by the characteristic emission of free radicals from an organ of the patient; and comparing the rate of said photon detection, signifying the rate of free radical emission, with the expected rate of free radical emission from a healthy organ.

2. A method in accordance with claim 1 wherein said detecting step comprises detecting photons of electromagnetic radiation caused by the characteristic emission of singlet oxygen from an organ of the patient, and wherein said comparing step comprises comparing the rate of said photon detection, signifying the rate of singlet oxygen emission, with the expected rate of singlet oxygen emission from a healthy organ.

3. A method in accordance with claim 1, wherein said body organ is the lung, brain, liver, heart, kidney or intestine.

4. A method in accordance with claim 1, wherein said detecting step is accomplished by means of a detector sensitive to the wavelength of said photons to be detected, said detector being placed on the exterior body surface of the patient adjacent said organ so as to direct said photons which reach the detector after being transmitted through superficial layers of body tissue.

5. A method in accordance with claim 1, wherein said detecting step is accomplished by means of a detector sensitive to the wavelength of said photons to be detected, said detector being placed within a body cavity of the patient so as to be near said organ and so as to detect said photons which reach the detector after being transmitted through intervening layers of body tissue.

6. A method in accordance with claim 1, further including the steps of detecting photons of electromagnetic radiation caused by the characteristics emission of free radicals from the patient at a location distant from said organ being monitored, and comparing the rate of said photon detection from said organ with the amount of said photons detected at said second location.

7. A method in accordance with claim 2, further including the steps of detecting photons of electromagnetic radiation caused by the characteristic emission of singlet oxygen from the patient at a location distant from said organ being monitored, and comparing the rate of said photon detection from said organ with the amount of said photons detected at said second location.

8. A method in accordance with claim 6, wherein said second location is on an arm or leg.

9. A method in accordance with claim 2, wherein said photons being detected are photons at a wavelength of about 1268 nm.

10. A method in accordance with claim 1, wherein said photons are photons of wavelength shorter than 1268 nm emitted as a result of or in association with free radical emission and caused by dimol emission, peroxide breaking, or epoxide bond breaking.

11. A method for diagnosing or monitoring a diseased state in a patient which manifests itself in a manner which includes the characteristic emission of free radicals within an internal body organ of the patient, comprising:

detecting photons of electromagnetic radiation caused by the characteristic emission of free radicals from an organ of the patient; and comparing the rate of said photon detection, signifying the rate of free radical emission, with the expected rate of free radical emission from a healthy organ.

12. A method in accordance with claim 11 for diagnosing or monitoring a diseased state in a patient which manifests itself in a manner which includes the characteristic emission of singlet oxygen within an internal body organ of the patient, wherein said detecting step comprises detecting photons of electromagnetic radiation caused by the characteristic emission of singlet oxygen from an organ of the patient, and wherein said comprising step comprises comparing the rate of said photon detection, signifying the rate of singlet oxygen emission, with the expected rate of singlet oxygen emission from a healthy organ.

13. A method in accordance with claim 11, wherein said diseased state is paraquat poisoning, alcoholism, or hepatitis, and wherein said organ being monitored is the liver.

14. A method in accordance with claim 11, wherein said diseased state is stroke or heart-attack and said organ being monitored is the heart or brain.

15. A method in accordance with claim 11, wherein said diseased state is oxygen overdose and wherein said organ being monitored is the brain.

16. A method for monitoring and controlling the administration of oxygen therapy to an oxygen deprived patient, comprising:

detecting photons of electromagnetic radiation caused by the characteristic emission of singlet oxygen from an organ of the patient; and if an abnormal rate of photon detection occurs, signifying an abnormal rate of singlet oxygen emission, controlling the administration of oxygen therapy such that the singlet oxygen emissions return to normal.

17. A method in accordance with claim 16, wherein said detecting step is accomplished by means of a detector sensitive to the wavelength of said photons to be detected, said detector being placed on the exterior body surface of the patient adjacent said organ so as to detect said photons which reach the detector after being transmitted through superficial layers of body tissue.

18. A method in accordance with claim 16, wherein said detecting step is accomplished by means of a detector sensitive to the wavelength of said photons to be detected, said detector being placed within a body cavity of the patient so as to be near said organ and so as to detect said photons which reach the detector after being transmitted through intervening layers of body tissue.

19. A method in accordance with claim 16, wherein said oxygen therapy is the therapeutic administration of substantially pure oxygen and said controlling step comprises stopping or decreasing said administration of substantially pure oxygen until the singlet oxygen emissions return to normal.

* * * * *